United States Patent [19]

Rosenquist

[11] Patent Number: 4,604,434
[45] Date of Patent: Aug. 5, 1986

[54] AROMATIC POLYCARBONATE CROSSLINKED WITH AROMATIC BIS CYCLIC CARBONATE

[75] Inventor: Niles R. Rosenquist, Evansville, Ind.

[73] Assignee: General Electric Company, Mt. Vernon, Ind.

[21] Appl. No.: 688,244

[22] Filed: Jan. 2, 1985

[51] Int. Cl.[4] .................... C08G 63/76; C08G 63/62
[52] U.S. Cl. .................................. 525/462; 528/196
[58] Field of Search ........................ 525/462; 528/196

[56] References Cited

U.S. PATENT DOCUMENTS

| | | | |
|---|---|---|---|
| 3,221,025 | 11/1965 | Prochaska | 260/340.2 |
| 3,422,119 | 1/1969 | Prochaska | 260/340.2 |
| 4,407,995 | 10/1983 | Dick | 524/108 |
| 4,409,349 | 10/1983 | Ham | 524/108 |
| 4,446,296 | 5/1984 | Rosenquist | 525/462 |

FOREIGN PATENT DOCUMENTS 57360 8/1982 European Pat. Off. .

*Primary Examiner*—Harold D. Anderson
*Attorney, Agent, or Firm*—Martin B. Barancik

[57] ABSTRACT

A composition comprising an aromatic polycarbonate branched or crosslinked with a residue of a compound of the formula

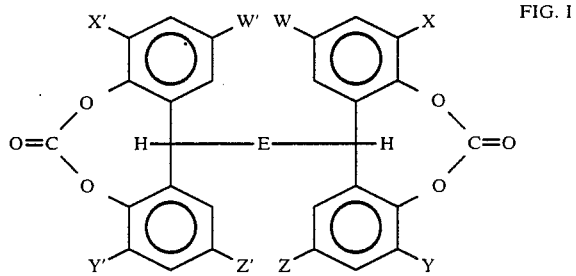

FIG. 1 wherein X, Y, X' and Y' are the same or different and are hydrogen or alkyl of one to about six carbon atoms, inclusive; W, W', Z and Z' are the same or different and are alkyl of one to about six carbon atoms, inclusive, and E is alkylene or alkylidene of two to about twelve carbon atoms, inclusive.

7 Claims, No Drawings

AROMATIC POLYCARBONATE CROSSLINKED WITH AROMATIC BIS CYCLIC CARBONATE

BACKGROUND OF THE INVENTION

Polycarbonates are well known polymers which have good property profiles, particularly with respect to impact resistance, electrical properties, dimensional rigidity and the like. These polymers are generally linear, but can be made with branched sites to enhance their properties in specific ways. Low levels of branching are generally incorporated into the resin by copolymerizing into the polymer backbone a tri or higher functional reagent to yield a thermoplastic polycarbonate resin with enhanced rheological properties and melt strength which make it particularly suitable for such types of polymer processing procedures as the blow molding of large, hollow containers and the extrusion of complex profile forms. Special manufacturing runs must be set aside to prepare these branched polycarbonate resins.

Sufficiently higher levels of branching sites in the resin will cause resin chains actually to join to each other to form partially or fully crosslinked resin networks which will no longer be thermoplastic in nature and which are expected to exhibit enhancements, over corresponding linear resins, in physical properties and/or in their resistance to abusive conditions, such as exposure to organic solvents. A wide variety of means have been employed to produce crosslinking in polycarbonate resin. These generally involve the incorporation of a suitably reactive chemical group either into the resin chain at its time of manufacture or as an additive to the resin after manufacture, or both. These reactive groups and the reactions they undergo are generally dissimilar from those characteristic of polycarbonate resin itself and are therefore prone to have detrimental side effects on the physical and/or chemical properties of the polymer. The conventional test used to judge the success of these means for crosslinking is to observe the formation of gels due to the crosslinked material when a resin sample is mixed with a solvent, such as methylene chloride, in which normal linear polycarbonate resin is highly soluble.

A new method has been discovered to prepare branched or crosslinked polycarbonate resin. This approach involves the use of an additive to the resin which has structure and reactivity very similar to that of the polycarbonate resin repeat unit itself. Thus, it offers the dual advantages of allowing the branch sites to be incorporated into standard linear resin subsequent to the manufacture of the resin and of providing this branching or crosslinking by a method which produces residual structural groups in the final composition which are expected to be physically and chemically compatible with the resin.

DESCRIPTION OF THE INVENTION

In accordance with the invention, there is an aromatic polycarbonate crosslinked with a residue of a compound of the formula

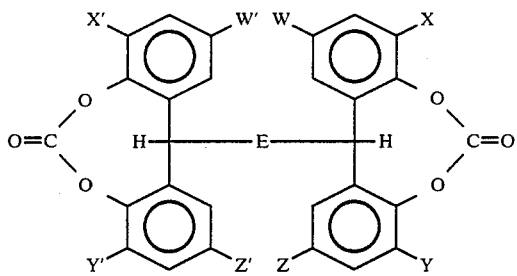

FIG. I wherein X, Y, X' and Y' are the same or different and are hydrogen or alkyl of one to about six carbon atoms, inclusive; W, W', Z and Z' are the same or different and are alkyl of one to about six carbon atoms, inclusive, and E is alkylene or alkylidene of two to about twelve carbon atoms, inclusive.

Another aspect of the invention is the compounds of the formula of FIG. I.

A further aspect of the invention is the precursor of the compounds of FIG. I, the compounds of the formula below

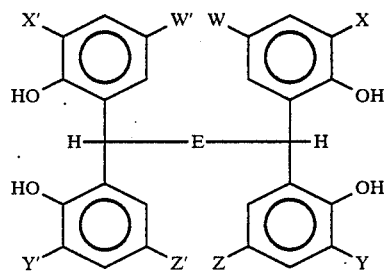

FIG. II wherein X, X', Y, Y', W, W', Z, Z' and E are the same as in FIG. I.

Alkyl of one to six carbon atoms, includes normal and branched alkyl, i.e. methyl, ethyl, propyl, butyl, pentyl, hexyl, isopropyl, isobutyl, tert.butyl, neopentyl and 2,3-dimethylbutyl and the like. Normal alkyl are preferred. Alkyl of one to three carbon atoms are also preferred. Alkylene of two to twelve carbon atoms, inclusive include normal and branched such as ethylene, propylene, butylene, isobutylene, 2,3- dimethylbutylene, hexylene, dodecylene and the like. Alkylidene include isopropylidene, 3,3-decylidene and the like. Alkylene and alkylidene of 2 to 6 carbon atoms are preferred.

The phenols of FIG. II are readily prepared by a conventional hydrochloric acid/mercaptan catalyzed condensation of an E dialdehyde with an appropriately W and X substituted phenol. Examples of such phenols include the p-cresols, 2,4-dimethylphenol and 2-ethyl4-butylphenol. When only one phenol is used in the reaction, W=Z=W'=Z' and X=Y=X'=Y'. When two different phenol starting materials are used, the substituents will vary depending on the phenol, per se, the proportions of the specific phenol and the rapidity of reaction with the aldehyde. The reaction can be carried out at an elevated temperature, i.e. from about 30° to about 100° C., preferably 40° to about 60° C. The acid is preferably anhydrous. The mercaptan is present as a catalyst in appropriate quantities.

The bis cyclic carbonates of FIG. I are readily prepared from the tetraphenols of FIG. II under standard conditions. For example the standard method of interfacially preparing polycarbonate is also applicable to preparing the bis cyclic carbonates, that is, the use of aqueous caustic, methylene chloride, phosgene, and triethylamine. Alternatively, the addition of a pyridine/methylene chloride solution of the tetraphenol to phosgene in methylene chloride can be employed. Standard work-up conditions such as washing and solvent removal yields a solid from which product is isolated by addition of an appropriate solvent such as toluene. Product precipitates therefrom. Raising the temperature to the reflux temperature of the pyridine/methylene chloride system improves the yield. When toluene is used as a solvent with a reaction temperature of 85° C., the reaction rate is accelerated substantially.

Standard aromatic polycarbonates are crosslinked with the biscyclic carbonates of FIG. I through conventional transesterification reaction systems using transesterification catalysts. Aromatic polycarbonates are made in the usual manner replete in the literature with the standard dihydric phenols such as bisphenol-A, o,o'o,o'-tetrabromo bisphenol-A, o,o',o,o'-tetra alkyl bisphenol-A and the like. The phrase aromatic polycarbonate includes aromatic copolyestercarbonate as well, described in Goldberg U.S. Pat. No. 3,169,121 incorporated by reference. Bisphenol-A polycarbonate is preferred.

The transesterification reaction utilized in the crosslinking is catalyzed by basic type catalysts usually employed in transesterification reactions, for example, oxides, hydrides, hydroxides or amides of the alkali or alkaline earth metals as well as basic metal oxides such as zinc oxides, salts of weak acids such as lithium stearate and organotitanium, organoaluminums and organotins such as tetraoctyltitanate. Because of potential steric hinderance it is preferred to use catalyst with less bulky groups, e.g. the lithium stearate as opposed to the tetraoctyl titanate.

The crosslinking is carried out by reacting the bis cyclic carbonates with the aromatic polycarbonate in the melt form in the presence of catalytic quantities of a transesterification catalyst. One of the benefits of using a cyclic carbonate is that there should be significantly less fragments of the polycarbonate chain present. The cyclic carbonate opens up thus allowing addition at either side of the carbonate group. This allows formation of structures of the following type.

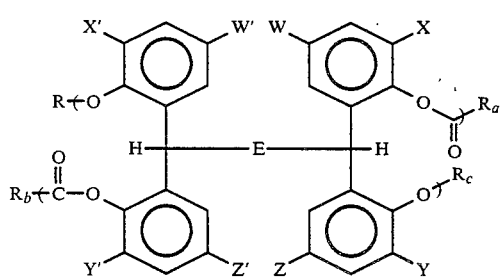

FIG. III wherein X, Y, X' and Y' are the same or different and are hydrogen or alkyl of one to about six carbon atoms, inclusive; W, W', Z and Z' are the same or different and are alkyl of one to about six carbon atoms, inclusive, E is alkylene or alkylidene of two to about twelve carbon atoms, inclusive; and R, $R_a$, $R_b$ and $R_c$ represent polycarbonates of various chain lengths. The minimum temperature of the reaction is sufficiently high to create a melt of the reactants. Such a temperature is achieved in an extruder or a molding machine such as an injection or compression molder normally employed for extruding or molding polycarbonate.

The final physical form of the crosslinked polycarbonate is at least partially dependent upon the quantity of bis cyclic carbonate present. If desired gel like forms, usually a high crosslinked thermoset material, can be avoided by utilizing relatively small quantities of the bis cyclic carbonates. The gels occur when greater quantities of the biscyclic carbonates are present. Also of significance is the reaction temperature and time.

Below are specific examples of the invention. These examples are intended to exemplify rather than narrow the inventive scope.

EXAMPLE 1

PREPARATION OF TETRAPHENOLS OF FIG. II

A. Preparation of the tetraphenol wherein W=Z=W'=Z'=methyl and X=Y=X'=Y'=hydrogen.

A 2000 ml four-neck flask was fitted with a mechanical stirrer, a gas inlet tube, a dropping funnel and a drying tube which had a nitrogen purge line passing past its outlet. The flask was placed in a 50° to 55° C. water bath. To the flask was added 1000 g (9.25 moles) of melted p-cresol. The flask was purged with nitrogen, then anhydrous hydrogen chloride was introduced until the p-cresol was saturated with it, then 2 ml of mercaptoacetic acid was added. With good agitation and continuous slow addition of hydrogen chloride, 256 g (1.28 mole) of a 50% aqueous solution of glutaric dialdehyde was added dropwise over 3 hours. During the addition of the aldehyde, a precipitate began to form and by the end of the addition the reaction mixture had become a thick paste. The water bath was then removed and the reaction mixture allowed to stand 3 days at room temperature. Volatiles were then removed with a water aspirator vacuum and a water layer which had formed on the surface of the mixture was removed by decanting. Toluene was then added to the flask and the mixture stirred until it formed a uniform slurry. The mixture was transferred to a larger flask where it was mixed with additional toluene to a final total volume of 4000 ml. The precipitate was collected by vacuum filtration and washed with an additional 1400 ml toluene. The resulting hard paste was washed twice with 1500 ml water, with a Waring blender being used initially to produce a uniform aqueous slurry. The final pH of the water filtrate was 4 to 5. The sample was dried in a vacuum dessicator (about 1 mm) to yield 405 g (65%) of a white powder (mp 220° to 228° C.).

B. Preparation of the tetraphenol wherein W=X=Y=Z=W'=X'=Y'=Z'=methyl.

A 500 g sample of 25% aqueous glutaric dialdehyde was extracted five times with 250 ml portions of methylene chloride and the combined extracts dried over MgSO4, filtered and the solvent partially removed on a rotary evaporator to yield 200 ml of a glutaric dialdehyde in methylene chloride solution. By nmr analysis, the solution was found to contain approximately 48 g (0.48 mole) of glutaric dialdehyde.

A 1000 ml four-neck flask was fitted with a mechanical stirrer, a gas inlet tube, a dropping funnel and a drying tube which had a nitrogen purge line passing past its outlet. The flask was placed in a 60° C. water bath. To the flask was added 489 g (4.0 mole) of 2,4- dimethylphenol. The flask was purged with nitrogen, then anhydrous HCl was added until saturation, then 1.0 ml of mercaptoacetic acid was added. With good agitation and continuous slow addition of HCl, the glutaric dialdehyde solution was added dropwise over three hours. A precipitate began to form after about 130 ml of the solution had been added. The reaction mixture was allowed to stand at room temperature for 16 hours, then it was slurried in 1200 ml of toluene, vacuum filtered and the precipitate re-slurried in 500 ml toluene, filtered and allowed to air dry. The resultant powder was washed four times with 500 ml distilled water, then two times with 250 ml toluene. The sample was dried in a vacuum dessicator (about 1 mm) to yield 242 g (91%) of a white powder (mp 236° to 242° C.).

EXAMPLE 2

PREPARATION OF BIS CYCLIC CARBONATES OF FIG. I $A_1$ Preparation of the bis cyclic carbonate of the tetraphenol of A above by the methylene chloride procedure.

A 2000 ml four-neck flask was fitted with a mechanical stirrer, a gas inlet tube, a dry ice condenser which had its outlet connected through a drying tube to a caustic scrubber and an inlet tube about an inch long connected through polypropylene tubing to a liquid metering pump ("Lab Pump, Jr.", #RHSY, Fluid Metering, Inc.) to which was connected an addition funnel. A solution of 74.5 g (0.15 mole) the tetraphenol of Example 1A and 55 ml (0.68 mole) of pyridine diluted to a total volume of 300 ml with methylene chloride was placed in the addition funnel. 1.25 liters of methylene chloride was placed in the flask. With the flash in a 10° C. water bath, 34 g (0.34 mole) of phosgene was added at 1 g/min. The bath was then warmed to 38° to 40° C. and, with vigorous stirring, the solution was added dropwise over a period of 8 hours. The flask was then allowed to cool to room temperature and the reaction mixture allowed to stand 16 hours, during which time large crystals of pyridinium hydrochloride formed. The solution was decanted from the crystals, washed three times with 400 ml distilled water, dried over MgSO4 and filtered. The solvent was removed on a rotary evaporator to yield a white paste which was placed under a 0.5 mm vacuum for 16 hours to yield a hard, brittle solid. The solid was broken up and stirred with 60 ml toluene to yield a uniform slurry which upon vacuum filtration yielded a white powder. The powder was washed a second time with 60 ml toluene, then twice with 60 ml methanol, then dried under vacuum to yield 36 g (44%) of a fine white powder (mp 269°–276° C.).

$A_2$ Preparation of the bis cyclic carbonate of A above by the toluene procedure. The apparatus was set up as described above for the methylene chloride procedure.

A solution of 74.5 g (0.15 mole) of the tetraphenol of Example 1A and 55 ml (0.68 mole) pyridine diluted to a total volume of 200 ml with methylene chloride was placed in the addition funnel. 1.25 l of toluene was placed in the flask. With the flask in a 10° C. water bath 5 g of phosgene was added at 1 g/min. The water bath temperature was then raised to 85° C. and over a period of 60 minutes with vigorous stirring the solution was added dropwise with simultaneous addition of phosgene at 0.5 g/min (35 g, 0.35 mole total phosgene). A white precipitate formed in the reaction during the addition. After allowing the reaction mixture to cool to room temperature and to stand 16 hours, the precipitate, which was a mixture of product and pyridinium hydrochloride, was collected by vacuum filtration and dried to a white powder under vacuum. (Removal of solvent from the filtrate on a rotary evaporator yields a viscous oil and no additional precipitate). The powder was washed twice with 500 ml water, then once with 150 ml methanol, then dried under vacuum to yield 29 g (35%) of a fine, white powder (mp 260° to 277° C.).

B. Preparation of the bis cyclic carbonate of the tetraphenol of Example 1B.

A 2000 ml four-neck flask was fitted with a mechanical stirrer, a pH probe, a gas inlet tube and a Claissen adapter to which was attached a dry ice condenser and an aqueous caustic inlet tube. To the flask was added 900 ml methylene chloride, 560 ml distilled water, 3.4 ml triethylamine, and a 22 g (0.04 mole) portion of tetraphenol of Example 1B. Phosgene was then introduced into the flask at 1 g/min for 50 minutes, with simultaneous addition at 5 minute intervals of additional 22 g portions of the tetraphenol (total of 50 g (0.5 mole) of phosgene and 220 g (0.4 mole) of tetraphenol). The pH was maintained at 9 to 11 with addition of 25% aq NaOH. The methylene chloride layer was separated from the brine layer, washed once with 350 ml of 3% aqueous HCl, three times with 350 ml distilled water, dried over MgSO4, filtered and the solvent removed on a rotary evaporator to yield a solid residue. The solid was washed twice with 200 ml portions of acetone, then recrystallized from toluene to yield 99 g (45%) of a white powder (mp 231.5° to 235.5° C.).

EXAMPLE 3

Preparation of crosslinked polycarbonates.

2.5 g (0.01 moles) of bisphenol-A polycarbonate powder (intrinsic viscosity of 0.49–0.52 in methylene chloride at 25° C.) was contacted with $1.0 \times 10^{-5}$ mole catalyst (0.1 mole %) and 2 mole % or 5 mole % bis cyclic carbonate at 300° C. under $N_2$ for a period of twenty minutes with thorough stirring of the melt. The results are shown below. In addition to these samples, five separate controls were run at the same time and temperature-polycarbonate alone, polycarbonate plus tetraoctyl titanate (TOT), polycarbonate plus lithium stearate (LiST), polycarbonate plus Example 2A bis cyclic carbonate, and polycarbonate plus Example 2B bis cyclic carbonate. No gels, as positively observed in the Table below were formed with any of the control formulations.

TABLE 1

| BIS CYCLIC CARBONATE | | % GEL* | |
|---|---|---|---|
| Example | Quantity, mole % | TOT | LiST |
| 2A | 2 | 23 | 25 |
| 2A | 5 | 57 | 47 |
| 2B | 2 | 5 | 25 |
| 2B | 5 | 4 | 52 |

*Quantity of gels was determined by swelling the resin "blobs" produced in methylene chloride, filtering and washing with additional methylene chloride.

What is claimed is:

1. A composition comprising an aromatic polycarbonate crosslinked with a residue of a compound of the formula

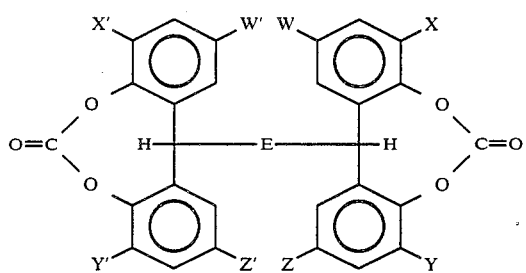

wherein X, Y, X' and Y' are the same or different and are hydrogen or alkyl of one to about six carbon atoms, inclusive; W, W', Z and Z' are the same or different and are alkyl of one to about six carbon atoms, inclusive, and E is alkylene or alkylidene of two to about twelve carbon atoms, inclusive.

2. The composition in accordance with claim 1 wherein W is equal to Z is equal to W' is equal to Z' is equal to methyl and X is equal to Y is equal to X' is equal to Y' is equal to hydrogen.

3. The composition in accordance with claim 1 wherein W is equal to X is equal to Y is equal to Z is equal to W' is equal to X' is equal to Y' is equal to Z' is equal to methyl.

4. The composition in accordance with claim 1 wherein E is alkylidene or alkylene of 2 to 6 carbon atoms.

5. The composition in accordance with claim 4 wherein E is normal alkylene of three carbon atoms.

6. The composition in accordance with claim 2 wherein E is normal alkylene of three carbon atoms.

7. The composition in accordance with claim 3 wherein E is normal alkylene of three carbon atoms.

* * * * *